(12) United States Patent
Hong

(10) Patent No.: US 10,072,837 B2
(45) Date of Patent: Sep. 11, 2018

(54) LIGHTING BOX

(71) Applicant: Soon Chang Hong, Seoul (KR)

(72) Inventor: Soon Chang Hong, Seoul (KR)

( * ) Notice: Subject to any disclaimer, the term of this patent is extended or adjusted under 35 U.S.C. 154(b) by 0 days.

(21) Appl. No.: 15/579,888

(22) PCT Filed: Jun. 17, 2016

(86) PCT No.: PCT/KR2016/006436
§ 371 (c)(1),
(2) Date: Dec. 5, 2017

(87) PCT Pub. No.: WO2016/208913
PCT Pub. Date: Dec. 29, 2016

(65) Prior Publication Data
US 2018/0172263 A1    Jun. 21, 2018

(30) Foreign Application Priority Data
Jun. 23, 2015 (KR) .................. 20-2015-0004184 U

(51) Int. Cl.
*F21V 33/00* (2006.01)
*A61L 9/12* (2006.01)
(Continued)

(52) U.S. Cl.
CPC ............ *F21V 33/0004* (2013.01); *A61L 9/12* (2013.01); *F21S 9/02* (2013.01); *F21V 23/0492* (2013.01);
(Continued)

(58) Field of Classification Search
CPC .... F21V 33/0004; F21V 23/0492; F21S 9/02; A61L 9/12; A61L 2209/111; G10F 1/06; F21Y 2115/10; F21W 2121/00
See application file for complete search history.

(56) References Cited

U.S. PATENT DOCUMENTS 3,937,320 A * 2/1976 Chao ...................... A45C 11/16
                                                           206/216
5,980,062 A * 11/1999 Bell ....................... F21V 33/008
                                                           362/154
(Continued)

FOREIGN PATENT DOCUMENTS

CN   101569453   11/2009
JP   06-308584   11/1994
(Continued)

*Primary Examiner* — Sonji Johnson
(74) *Attorney, Agent, or Firm* — IPLA, P.A.; James E. Bame

(57) ABSTRACT

A lighting box having LED units in the interior of a body thereof to allow an elegant exterior appearance for the lighting box to be designed, and having a switch and a control unit so that the LED units are turned on and off with the opening and closing of the box The lighting box comprises a body; a control panel attached on an inner surface of the body; a battery unit attached to the control panel; LED units driven by the battery unit and located inside the body and attached to the control panel; an LED cover for covering the LED units; a switch, attached to the body, for controlling the operations of the LED units; a cover which covers the body; and a control unit, disposed on the cover, for controlling the switch being turned on and off.

1 Claim, 4 Drawing Sheets

(51) Int. Cl.
  *F21S 9/02* (2006.01)
  *G10F 1/06* (2006.01)
  *F21V 23/04* (2006.01)
  *F21W 121/00* (2006.01)
  *F21Y 115/10* (2016.01)

(52) U.S. Cl.
  CPC ........... *G10F 1/06* (2013.01); *A61L 2209/111* (2013.01); *F21W 2121/00* (2013.01); *F21Y 2115/10* (2016.08)

(56) References Cited

U.S. PATENT DOCUMENTS 7,086,751 B2 * 8/2006 Clark .................. A47F 11/10
  362/125
9,743,494 B1 * 8/2017 McCrory ........... H05B 37/0227

FOREIGN PATENT DOCUMENTS

| KR | 2002065530000 | 10/2000 |
| KR | 20070000275 | 3/2007 |

* cited by examiner

LIGHTING BOX

BACKGROUND

The present invention relates to a lighting box, and more particularly, to a lighting box having LED units in the interior of a body thereof so that the LED units are turned on and off with the opening and closing of the box to achieve an elegant exterior design for the lighting box.

BACKGROUND ART

Generally, a variety of boxes, such as package boxes, storage boxes, and the like, are used, and in more detail, package boxes are used to accommodate birthday, graduation, wedding anniversary, and admission gifts, and the storage boxes are used to store various items like clothes, jewelry, tools, and so on.

Such boxes are used only to keep the gifts or items therein, and accordingly, it is hard to independently use them for specific impressions or events.

So as to solve the above-mentioned problems, functional boxes having various functions have been recently developed.

One example of conventional functional boxes is disclosed in Korean Utility Model Registration No. 20-0331003, wherein the functional box includes a through hole formed to a given shape on one surface thereof to check an item disposed therein and a lighting device having a lamp located at a given position around the through hole to emit light to the interior of the box if a switch is turned on by means of a battery.

According to the conventional functional box, however, the light emitted from the lamp is directly penetrated into a user's eyes to cause eye fatigue, so that his or her vision may be decreased or he or she may get side effects like visual hallucinations on his or her eyes.

SUMMARY OF THE INVENTION

Accordingly, the present invention has been made in view of the above-mentioned problems occurring in the prior art, and it is an object of the present invention to provide a lighting box having LED units in the interior of a body thereof, thereby achieving an elegant exterior design for the lighting box.

It is another object of the present invention to provide a lighting box having a switch and a control unit disposed therein so that LED units are turned on and off with the opening and closing of the box.

It is still another object of the present invention to provide a lighting box having an LED cover for LED units to allow light emitted from the LED units to be scattered, thereby providing soft light.

To accomplish the above-mentioned objects, according to the present invention, there is provided a lighting box including: a body; a control panel disposed on the inner bottom of the body; a battery unit coupled to the control panel; LED units operating by the battery unit and disposed inside the body in such a manner as to be coupled to the control panel; an LED cover for covering the LED units; a switch coupled to the body to control the operations of the LED units; a cover coupled to the body; and a control unit disposed on the cover to control on/off operations of the switch.

According to the present invention, desirably, the lighting box further includes an air freshener operating by means of the battery unit and the switch.

According to the present invention, desirably, the lighting box further includes an orgel operating by means of the battery unit and the switch.

According to the present invention, desirably, the lighting box further includes an air freshener and an orgel operating by means of the battery unit and the switch.

According to the present invention, desirably, the orgel operates electromagnetically by means of the battery unit or operates spirally.

According to the present invention, the lighting box is provided with the LED units in the interior thereof, thereby achieving an elegant exterior design.

According to the present invention, in addition, the lighting box is provided with the switch and the control unit disposed therein so that the LED units are turned on and off with the opening and closing of the box.

According to the present invention, further, the lighting box is provided with the LED cover for the LED units to allow light emitted from the LED units to be scattered, thereby providing soft light.

EXPLANATIONS ON REFERENCE NUMERALS OF DRAWING

Figure 1:
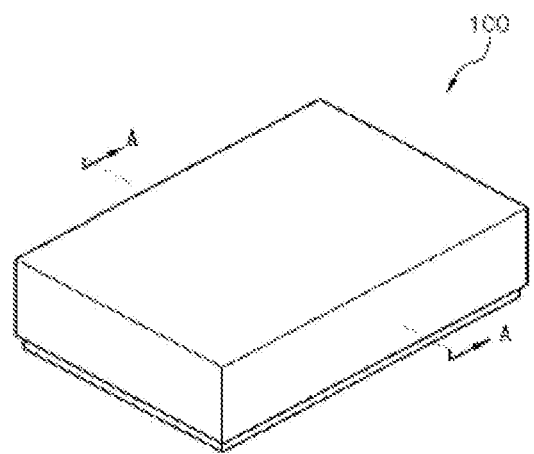
FIG. 1 is a perspective view showing a lighting box according to a first embodiment of the present invention.

100,200,300,400: lighting box
110,210,310,410: body
120,220: control panel
121: LED insertion hole
120,230,330,430: battery unit
140,240,340,440: LED unit
150,250,350,450: LED cover
160,260,360,460: switch
170,270,370,470: cover
180,280,380,480: control unit
290,490: orgel
391,491: air freshener

DETAILED DESCRIPTION OF THE INVENTION

According to the present invention, a lighting box includes: a body configured to be a box open on top thereof;

a control panel serving as an instrument panel, on which control instruments are collected and controlled, disposed on the inner bottom of the body, and having a battery insertion hole and LED insertion holes formed on top thereof; a battery unit inserted into the battery insertion hole in such a manner as to be electrically connected to the control panel; LED units inserted into the LED insertion holes in such a manner as to be electrically connected to the control panel to emit light with the electricity supplied from the battery unit; an LED cover unit made of any one material selected from paper, cloth, and cotton to allow the light emitted from the LED units to be scattered; a switch disposed on the body to control the operations of the LED units; a cover coupled to the top of the body to cover the open portion of the body; a control unit disposed on the cover to control the on/off operations of the switch, so that in a state where the cover is coupled to the body, the switch is turned off, and in a state where the cover is separated from the body, the switch is turned on; an air freshener operating by means of the battery unit and the switch; and an orgel operating by means of the battery unit and the switch in an electromagnetic or spiral manner.

Hereinafter, an explanation on a lighting box according to the present invention will be given in detail with reference to the attached drawing.

FIG. 1 is a perspective view showing a lighting box 100 according to a first embodiment of the present invention.

As shown, the lighting box 100 is means for containing an item therein, which is made of wood, board, glass, plastic, rubber, metal, and so on.

Figure 2:
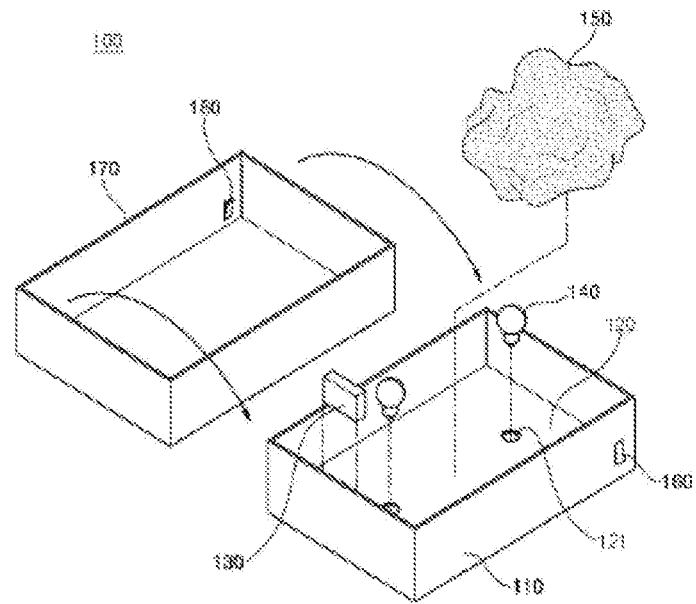
FIG. 2 is an exploded perspective view showing the lighting box of FIG. 1.
Figure 3:
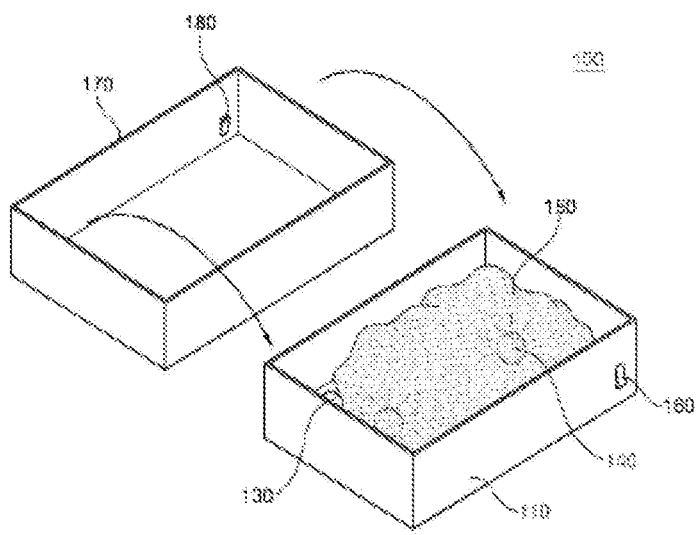
FIG. 3 is a perspective view showing the use state of the lighting box of FIG. 1.
Figure 4:
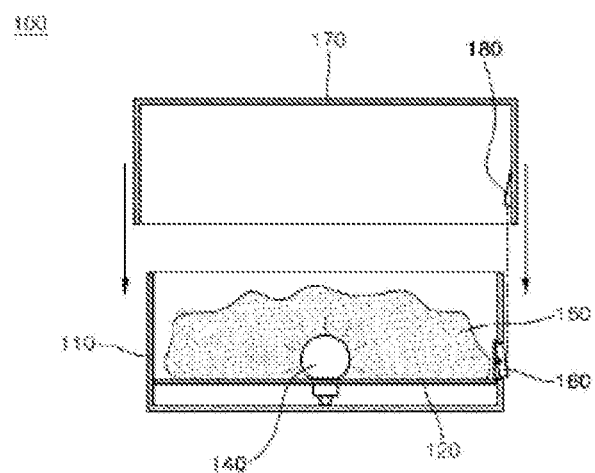
FIG. 4 is a sectional view taken along the line A-A of FIG. 1.

Now, an explanation on the structure of the lighting box 100 according to the first embodiment of the present invention will be in more detail given with reference to FIGS. 2 to 4.

FIG. 2 is an exploded perspective view showing the lighting box of FIG. 1.

As shown, the lighting box 100 includes a body 110, a control panel 120, a battery unit 130, LED units 140, an LED cover unit 150, a switch 160, a cover 170, and a control unit 180.

In more detail, the body 110 is configured to be a box open on top thereof to accommodate an item therein in such a manner as to allow the control panel 120 to be coupled to the inner bottom thereof.

The control panel 120 is an instrument panel, on which control instruments are collected and easily controlled, and the control panel 120 is coupled to the inside of the body 110 in such a manner as to be coupled to the battery unit 130 and the LED units 140. Further, the control panel 120 includes a battery insertion hole (not shown) for inserting the battery unit 130 and LED insertion holes 121 for inserting the LED units 140.

The LED units 140 include an ON/OFF switch (single pole switch) or optical sensor.

The LED cover unit 150 is made of a material capable of scattering light, such as paper, cloth, semi-transparent plastic, cotton, and so on and is adapted to cover the LED units 140, so that the light emitted from the LED units 140 is scattered.

The switch 160 is disposed on one surface of the body 110 in such a manner as to be coupled to the control panel 120 to control the operations of the LED units 140.

The cover 170 has a shape corresponding to the body 110 to cover the open top and edge surfaces of the body 110.

The control unit 180 is disposed on the cover 170 to control the on/off operations of the switch 160. An organic operating relationship between the control unit 180 and the switch 160 will be explained later with reference to FIG. 4.

FIG. 3 is a perspective view showing the use state of the lighting box of FIG. 1.

As shown, the battery unit 130 and the LED units 140 are coupled to the control panel 120 mounted in the interior of the body 110, and the tops of the LED units 140 are covered with the LED cover unit 150.

The battery unit 130 includes an electric current, and the electric current is transferred to the LED units 140 from the control panel 120 so that light is generated from the LED units 140.

The LED units 140 emit the light in accordance with the on/off operations of the switch 160, and the switch 160 is shielded by the control unit 180.

The cover 170 having the corresponding shape to the body 110 covers top of the body 110, and the control unit 180 is disposed at the inside of the cover 170 to control the operation of the switch 160 disposed on one surface of the body 110.

FIG. 4 is a sectional view taken along the line A-A of FIG. 1.

As shown, the open top of the body 110 is coupled correspondingly to the open bottom of the cover 170, and in the process of coupling the body 110 and the cover 170 to each other, the switch 160 is under the control of the control unit 180.

The control unit 180 is formed protrudingly from one surface of the inner side of the cover 170 so that when the cover 170 and the body 110 are coupled to each other, the control unit 180 is moved along one side of the switch 160 and gets in touch with the other side of the switch 160. In more detail, one side of the switch 160, that is, a position where the switch 160 is turned on, is always provided, and the other side of the switch 160, that is, a position where the switch 160 is turned off, is fixed by the control unit 180.

If the body 110 is covered with the cover 170, the switch 160 is turned off by means of the control unit 180, so that the LED units 140 are turned off. On the other hand, if the body 110 exists while being not covered with the cover 170, the switch 160 is always turned on, so that the LED units 140 are turned on.

Figure 5:
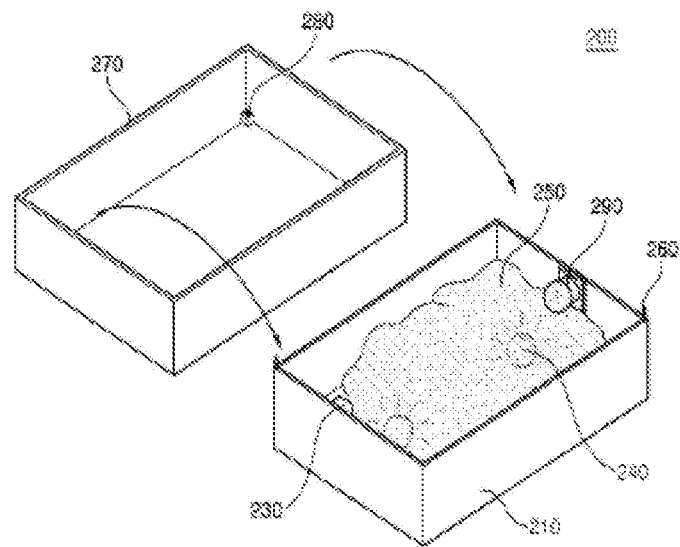
FIG. 5 is a perspective view showing the use state of a lighting box according to a second embodiment of the present invention.

FIG. 5 is a perspective view showing the use state of a lighting box 200 according to a second embodiment of the present invention.

As shown, the lighting box 200 includes a body 210, a control panel (not shown), a battery unit 230, LED units 240, an LED cover unit 250, a switch 260, a cover 270, a control unit 280, and an orgel 290.

The lighting box 200 as shown in FIG. 5 according to the second embodiment of the present invention is the same as the lighting box 100 as shown in FIGS. 2 to 4 according to the first embodiment of the present invention, except that the switch 260 and the control unit 280 are different in shape from the switch 160 and the control unit 180 and the orgel 290 is further disposed on the body 210.

The body 210 and the cover 270, which have corresponding shapes to each other, are coupled correspondingly to each other.

The switch 260 is located at top of one side edge of the body 210.

The control unit 280 is disposed at one surface of the inner side of the cover 270 adjacent to the switch 260 when the body 210 and the cover 270 are coupled to each other.

The orgel 290 is disposed between the body 210 and the control panel (not shown). When the electric current of the battery unit 230 is transferred to the LED units 240 and the orgel 290 through the control panel (not shown), light is emitted from the LED units 240, and sounds stored in the orgel 290 are transmitted to the outside.

The orgel 290 operates electronically by the electric current of the battery unit 230, but of course, it may operate spirally.

Figure 6:
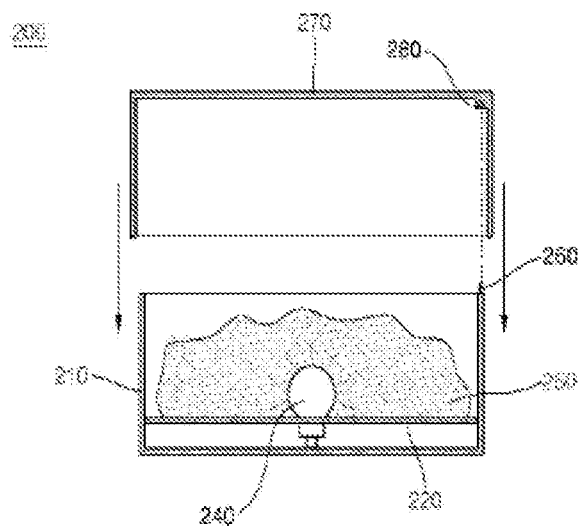
FIG. 6 is a sectional view showing the lighting box of FIG. 5.

FIG. 6 is a sectional view showing the use state of the lighting box 200 of FIG. 5, wherein the body 210 and the cover 270 are coupled to each other.

The lighting box 200 as shown in FIG. 6 according to the second embodiment of the present invention is the same as the lighting box 100 as shown in FIG. 4 according to the first embodiment of the present invention, except that the switch 260 and the control unit 280 are different in shape from the switch 160 and the control unit 180.

As shown, the switch 260 is disposed on the cover 210 to a form of a push button switch, and the switch 260 is always turned on. When the body 210 is coupled to the cover 270, the switch 260 is pressurized against the control unit 280 disposed on the cover 270 and is thus turned off.

By the way, the configuration, shape and organic coupling of the lighting box 200 as shown in FIGS. 5 and 6 are described already when the lighting box is explained with reference to FIGS. 1 to 4, and therefore, a detailed explanation on them will be avoided.

Figure 7:
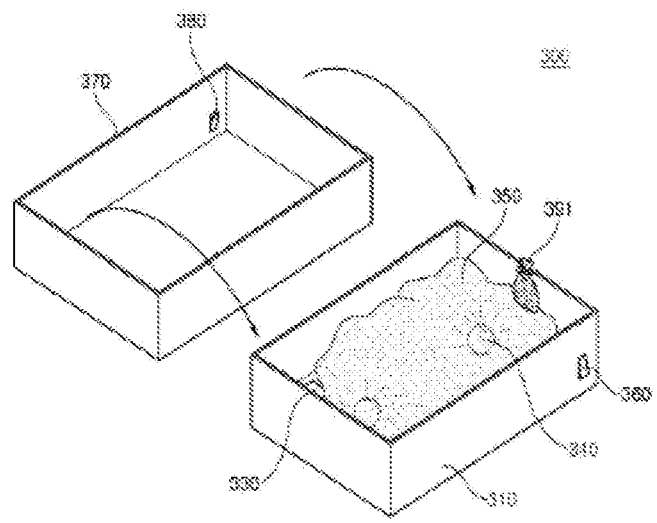
FIG. 7 is a perspective view showing the use state of a lighting box according to a third embodiment of the present invention.

FIG. 7 is a perspective view showing the use state of a lighting box 300 according to a third embodiment of the present invention.

As shown, the lighting box 300 includes a body 310, a control panel (not shown), a battery unit 330, LED units 340, an LED cover unit 350, a switch 360, a cover 370, a control unit 380, and an air freshener 391.

The lighting box 300 as shown in FIG. 7 according to the third embodiment of the present invention is the same as the lighting boxes 100 and 200 as shown in FIGS. 2 to 6 according to the first and second embodiments of the present invention, except that the switch 360 and the control unit 380 are different in shape from the switches 160 and 260 and the control units 180 and 280 and the air freshener 391 is further disposed on the body 310.

The air freshener 391 is disposed between the body 310 and the control panel (not shown). When the electric current of the battery unit 330 is transferred to the LED units 340 and the air freshener 391 through the control panel (not shown), light is emitted from the LED units 340. Also, the air freshener 391 stores a user's desired fragrance therein, and it is turned on/off in the same manner as the LED units 340. When the LED units 340 are turned on/off, the air freshener 391 is turned on/off at the same time.

By the way, the configuration, shape and organic coupling of the lighting box 300 as shown in FIG. 7 are described already when the lighting boxes are explained with reference to FIGS. 1 to 6, and therefore, a detailed explanation on them will be avoided.

Figure 8:
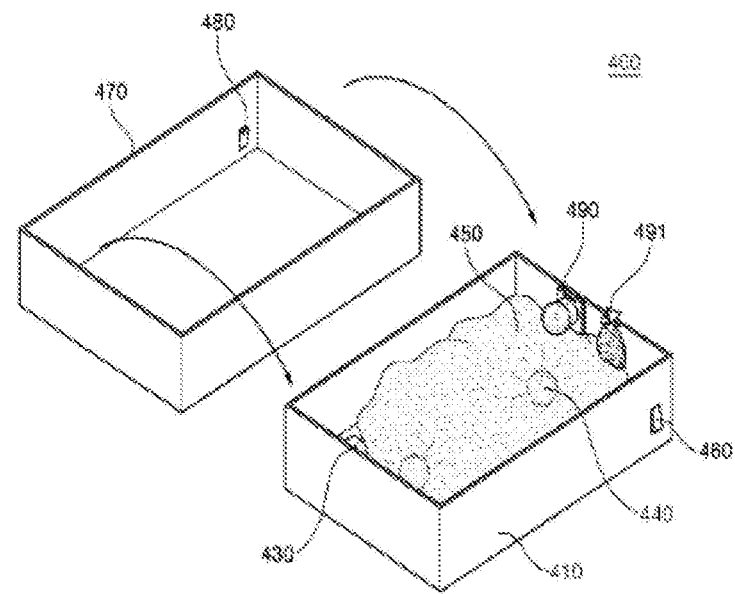
FIG. 8 is a perspective view showing the use state of a lighting box according to a fourth embodiment of the present invention.

FIG. 8 is a perspective view showing the use state of a lighting box 400 according to a fourth embodiment of the present invention.

As shown, the lighting box 400 includes a body 410, a control panel (not shown), a battery unit 430, LED units 440, an LED cover unit 450, a switch 460, a cover 470, a control unit 480, an orgel 490 and an air freshener 491.

The lighting box 400 as shown in FIG. 8 according to the fourth embodiment of the present invention is the same as the lighting boxes 100, 200 and 300 as shown in FIGS. 2 to 7 according to the first to third embodiments of the present invention, except that the switch 460 and the control unit 480 are different in shape from the switches 160, 260 and 360 and the control units 180, 280 and 380 and the orgel 490 and the air freshener 491 are further disposed on the body 410.

By the way, the configuration, shape and organic coupling of the lighting box 400 as shown in FIG. 8 are described already when the lighting boxes are explained with reference to FIGS. 1 to 7, and therefore, a detailed explanation on them will be avoided.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

INDUSTRIAL APPLICABILITY

According to the present invention, the lighting box includes the LED units in the interior thereof to provide an elegant exterior design, the switch and the control unit disposed therein so that the LED units are turned on and off with the opening and closing of the box, and the LED cover for the LED units to allow light emitted from the LED units to be scattered to provide soft light.

The invention claimed is:

1. A lighting box comprising:
a body configured to be a box open on top thereof;
a control panel serving as an instrument panel, on which control instruments are collected and controlled, disposed on the inner bottom of the body, and having a battery insertion hole and LED insertion holes formed on top thereof;
a battery unit inserted into the battery insertion hole in such a manner as to be electrically connected to the control panel;
LED units inserted into the LED insertion holes in such a manner as to be electrically connected to the control panel to emit light with the electricity supplied from the battery unit;
an LED cover unit made of any one material selected from paper, cloth, and cotton to allow the light emitted from the LED units to be scattered;
a switch disposed on the body to control the operations of the LED units;
a cover coupled to the top of the body to cover the open portion of the body;
a control unit disposed on the cover to control the on/off operations of the switch, so that in a state where the cover is coupled to the body, the switch is turned off, and in a state where the cover is separated from the body, the switch is turned on;
an air freshener operating by means of the battery unit and the switch; and
an orgel operating by means of the battery unit and the switch in an electromagnetic or spiral manner.

* * * * *